(12) United States Patent
Mitsumoto

(10) Patent No.: US 7,202,090 B2
(45) Date of Patent: Apr. 10, 2007

(54) HARDNESS MEASUREMENT REAGENT

(75) Inventor: Hiroyuki Mitsumoto, Matsuyama (JP)

(73) Assignee: Miura Co., Ltd., Matsuyama-shi (JP)

( * ) Notice: Subject to any disclaimer, the term of this patent is extended or adjusted under 35 U.S.C. 154(b) by 0 days.

(21) Appl. No.: 11/091,552

(22) Filed: Mar. 29, 2005

(65) Prior Publication Data
US 2005/0221499 A1 Oct. 6, 2005

(30) Foreign Application Priority Data
Mar. 30, 2004 (JP) .............................. 2004-099158

(51) Int. Cl.
*G01N 33/20* (2006.01)
*G01N 31/00* (2006.01)

(52) U.S. Cl. .............................. 436/73; 436/8; 436/18; 436/111; 436/131; 436/132; 436/79; 436/166; 252/408.1

(58) Field of Classification Search .............. 436/8, 436/18, 106, 111, 131, 132, 164, 166, 74, 436/79, 73; 252/408.1
See application file for complete search history.

(56) References Cited

U.S. PATENT DOCUMENTS 3,159,586 A * 12/1964 Wildenhayn ................. 436/79
3,240,717 A * 3/1966 Johnson ....................... 436/79
3,368,969 A * 2/1968 Palen .......................... 210/698
4,205,955 A * 6/1980 Sloat ........................... 436/79
6,190,611 B1 2/2001 Tachino et al.
6,599,748 B1 7/2003 Nakajima et al.
2006/0073999 A1* 4/2006 Sgargetta et al. ........... 510/220

FOREIGN PATENT DOCUMENTS

| GB | 967213 | * | 8/1964 |
| GB | 991298 | * | 5/1965 |
| JP | 2-82160 | * | 3/1990 |
| JP | 11-64323 A | | 3/1999 |
| JP | 2002-181802 A | | 6/2002 |
| JP | 2002-181803 A | | 6/2002 |
| RU | 2076322 | * | 3/1997 |

* cited by examiner

*Primary Examiner*—Maureen M. Wallenhorst
(74) *Attorney, Agent, or Firm*—Birch, Stewart, Kolasch & Birch, LLP

(57) ABSTRACT

To provide a hardness measurement reagent unaffected by an M alkalinity in hardness measurement. A hardness measurement reagent as a one-solution type reagent includes a dye chosen from Eriochrome Black T (EBT) and Calmagite, triethanolamine, a glycol compound, and a pH buffer, in which the pH buffer includes a combination of amines selected from primary amines and secondary amines and a salt of a weak base.

5 Claims, 3 Drawing Sheets

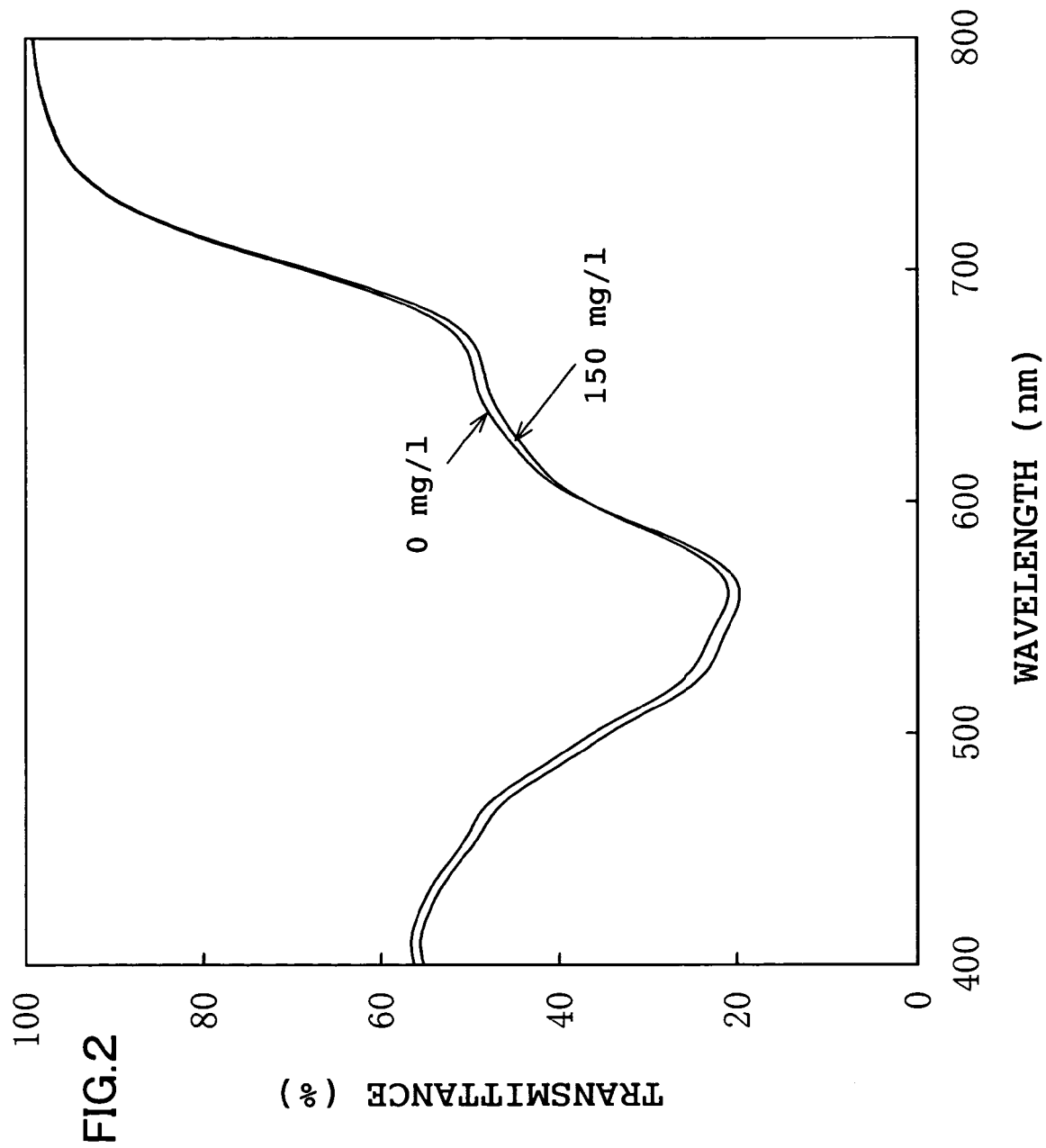

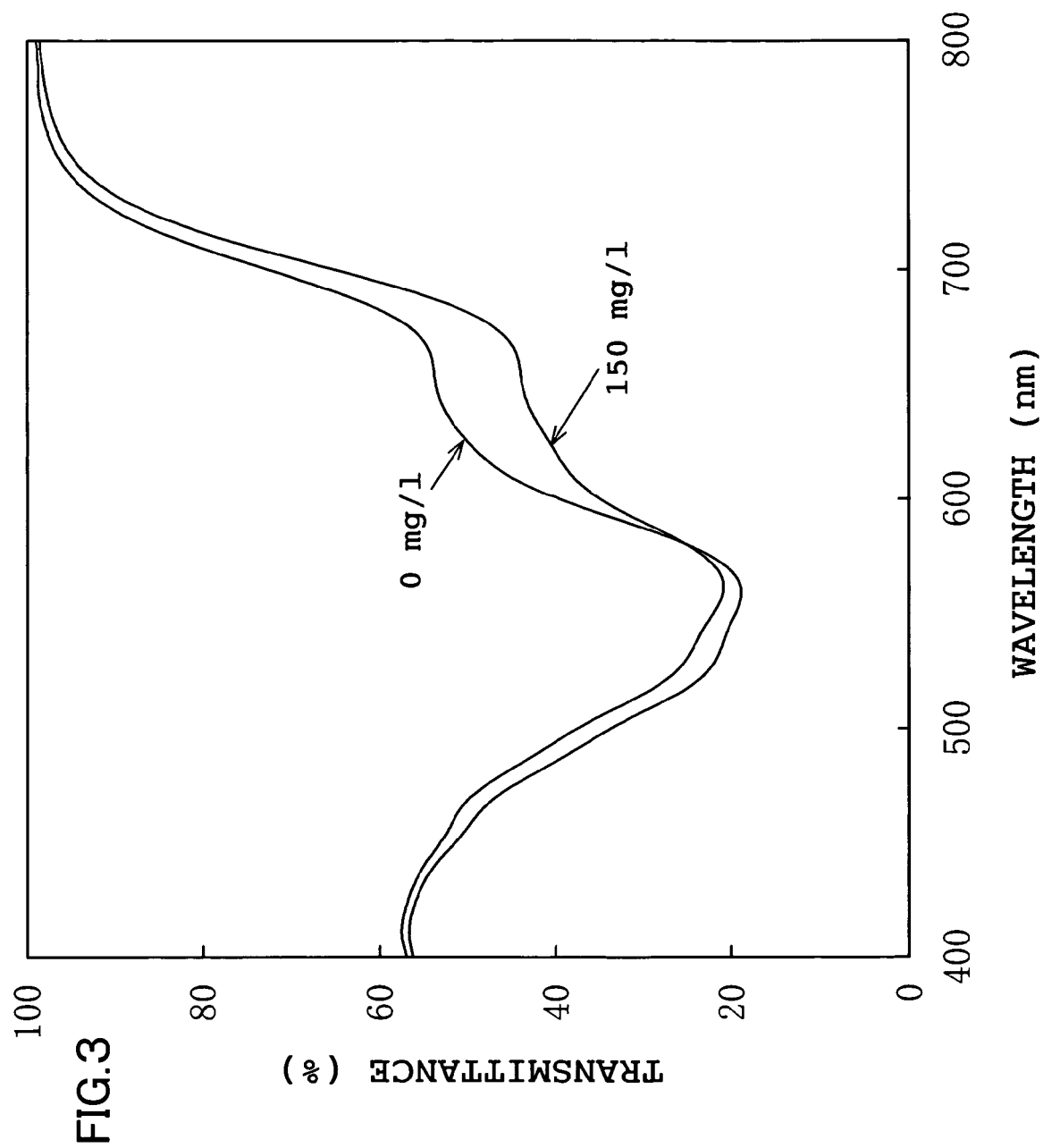

HARDNESS MEASUREMENT REAGENT

BACKGROUND OF THE INVENTION

1. Field of the Invention

The present invention relates to a hardness measurement reagent used for measuring a hardness of industrial water, daily life water, and the like.

2. Description of the Related Art

As is well known, a device for removing hardness components ($Ca^{2+}$ and $Mg^{2+}$) in raw water such as industrial water or daily life water is connected to a feed water line to cooling/heating equipment such as a boiler, a water heater, and a cooler from a need of prevention of scale deposition within the cooling/heating equipment. For example, a water softening device employing an ion-exchange resin is connected to a feed water line, to thereby replace the hardness components ($Ca^{2+}$ and $Mg^{2+}$) in raw water by $Na^+$ and supply the obtained softened water as feed water to the cooling/heating equipment.

In the case where the water softening device is used, degradation of the ion-exchange resin held inside the device or insufficient regeneration of the ion-exchange resin causes insufficient replacement of the hardness components in feed water by $Na^+$. Thus, an allowable hardness must be set in advance according to a hardness or the like of raw water in a region or place where the cooling/heating equipment is provided, and a hardness of the feed water passed through the water softening device must be measured periodically. A hardness of the feed water exceeding the upper limit (hereinafter, referred to as "control hardness") of an allowable value indicates hardness leakage. Thus, the ion-exchange resin is changed, regenerated, or the like to adjust the feed water within a predetermined hardness range.

There is disclosed a method of measuring a hardness of feed water involving, for example: adding a nonaqueous hardness measurement reagent containing as a dye Eriochrome Black T (EBT) to sample water sampled from feed water; and using a hue of the sample water as an index of a hardness (see JP 11-064323 A, JP 2002-181802 A, and JP 2002-181803 A). The hue of the sample water is qualitatively determined from an abundance ratio of a chelate compound formed through a reaction between hardness components and a dye in the hardness measurement reagent, to an unreacted (free) dye. To be specific, when EBT is used as a dye, a hue of sample water changes from an initial blue color to a bluish purple color (hereinafter, a hardness displaying a hue of a bluish purple color is referred to as a "color change starting point"), to a reddish purple color, and then to a red color (hereinafter, a hardness displaying a hue of a red color is referred to as a "color change end point") with increasing hardness of the sample water.

A control hardness is set in advance when the hardness leakage is detected by focusing on such a change in hue corresponding to a hardness of the sample water. Further, measuring conditions such as a mixing ratio of EBT in a hardness measurement reagent, an amount of the hardness measurement reagent added during measuring, and a volume of the sample water are determined such that the control hardness falls within a range between the color change starting point and the color change end point. Then, an actual measuring operation is conducted.

Thus, when the change in hue corresponding to a hardness of the sample water is used as an index of hardness leakage, a hue measuring method generally employs visual measuring through observation by humans or mechanical measuring through transmittance measurement or absorbance measurement. In the visual measuring, a change in hue of the sample water to a bluish purple color or to a red color indicates the hardness leakage. Further, in the mechanical measuring, a hardness is directly displayed on a measuring device based on a calibration curve showing a relationship between a hardness and a transmittance (or absorbance), and a hardness reaching the control hardness indicates the hardness leakage. In either measuring method, coloring of a dye is desirably not interfered with interfering substances in the sample water in order to display a hue corresponding to a hardness for reliable detection of the hardness leakage.

However, studies of the inventors of the present invention have confirmed that coloring of the sample water using a conventional hardness measurement reagent tends to be more interfered with a higher M alkalinity of the feed water. This tendency does not particularly cause problems in the visual measuring because the M alkalinity has a small effect on the hue of the sample water. However, the tendency results in a difference between an actual hardness and a measured hardness in the mechanical measuring, and thus improvements of the hardness measurement reagent have been desired for reliable detection of the hardness leakage of water having a high M alkalinity.

SUMMARY OF THE INVENTION

The present invention has been made in view of the above problems, and an object of the present invention is therefore to provide a hardness measurement reagent unaffected by an M alkalinity in hardness measurement.

The inventors of the present invention have conducted extensive studies for attaining the above object, and have found that coloring of a dye is interfered in feed water having a high M alkalinity because a pH of sample water having an reagent added does not increase to a target pH and that the above object can be attained by using a hardness measurement reagent mixed with a pH buffer having a higher buffer capacity than that of an M alkaline component. Thus, the inventors of the present invention have completed the present invention.

That is, a first aspect of the present invention relates to a hardness measurement reagent as a one-solution type reagent, including: a dye chosen from Eriochrome Black T (EBT) and Calmagite; triethanolamine; a glycol compound; and a pH buffer, in which the pH buffer is a combination of amines selected from primary amines and secondary amines and a salt of a weak base.

"One-solution type" means that a hardness measurement reagent is one solution which contains whole ingredients needed to determine the hardness in water, and that a hardness measurement reagent has multi function: as a dye (i.e. a hardness indicator), as a pH buffer, as a masking reagent, as a titrant solution and so on. When the hardness in water is determined by a hardness measurement reagent, no other reagent are needed; therefore a measuring procedure with a hardness measurement reagent is very simple.

A second aspect of the present invention relates to a hardness measurement reagent according to the first aspect of the present invention, in which the salt of a weak base includes a salt selected from the group consisting of an ammonium salt, a primary amine salt, and a secondary amine salt.

According to the hardness measurement reagent of the present invention, coloring of the dye is hardly interfered regardless of a level of the M alkalinity in the feed water, and the hardness leakage can be detected accurately particularly in mechanical measuring.

BRIEF DESCRIPTION OF THE DRAWINGS

In the accompanying drawings:

FIG. 2 is a diagram of transmittance spectra showing an effect of an M alkalinity using a hardness measurement reagent of Example 1; and FIG. 3 is a diagram of transmittance spectra showing an effect of an M alkalinity using a hardness measurement reagent of Comparative Example 1.

DETAILED DESCRIPTION OF THE INVENTION

Figure 1:
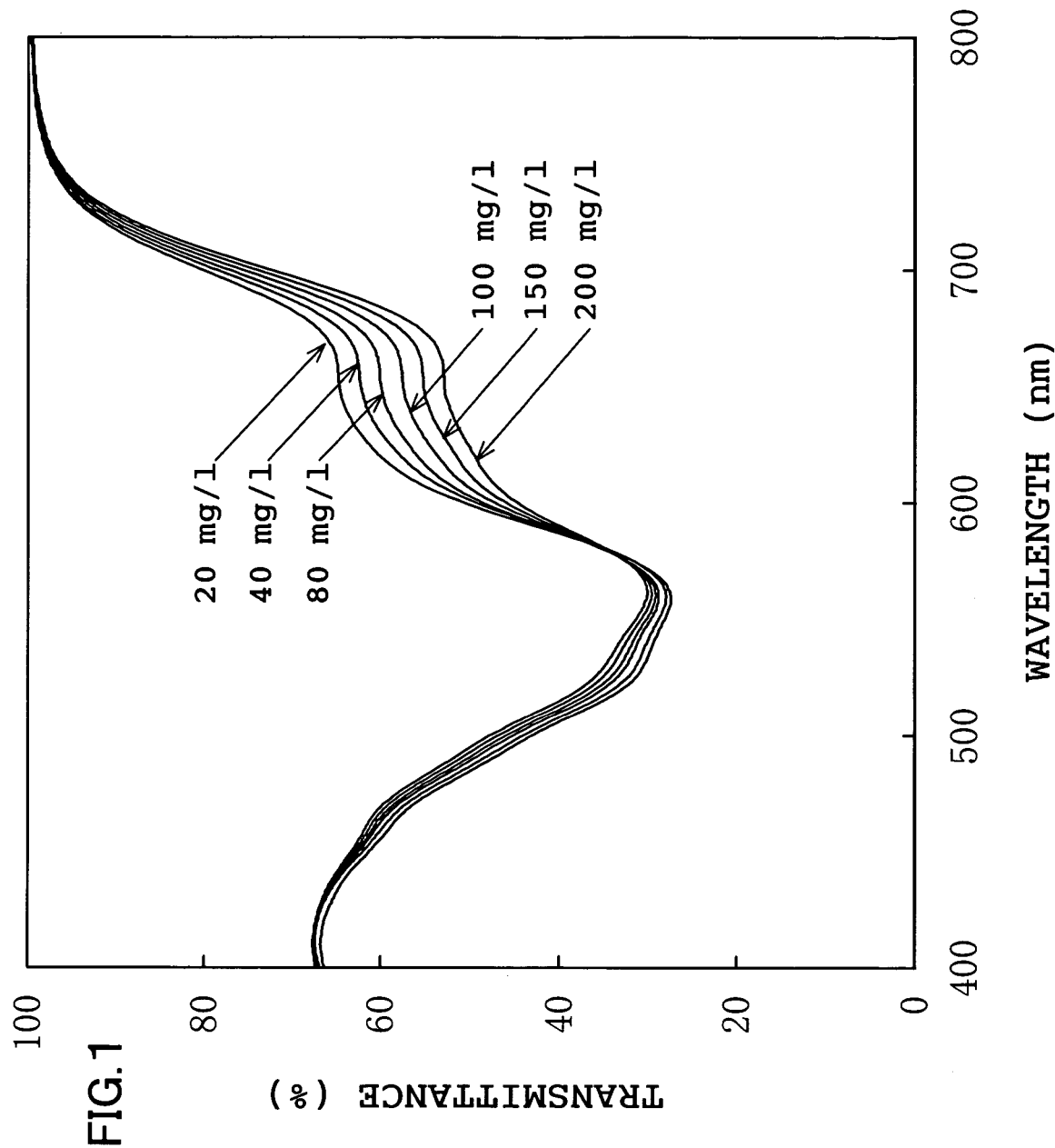
FIG. 1 is a diagram showing changes in transmittance spectra of standard solutions having different M alkalinities using a conventional hardness measurement reagent added thereto.

A hardness measurement reagent of the present invention is a one-solution type, nonaqueous reagent characterized by including a dye chosen from Eriochrome Black T (EBT) and Calmagite, triethanolamine, a glycol compound, and a pH buffer, in which the pH buffer is a combination of amines selected from primary amines and secondary amines and a salt of a weak base.

EBT or Calmagite is a dye clearly changing in color from a blue color to a red color by forming a chelate compound with hardness components in an alkaline pH range, and may be used alone or as a mixture. A mixing ratio of the dye is not particularly limited. The dye is used in a ratio of preferably 0.1 to 1.0 wt %, more preferably 0.1 to 0.5 wt % of the hardness measurement reagent from the viewpoint of coloring stability of sample water.

Triethanolamine is used for stabilizing the coloring of the dye by maintaining a pH of the sample water at about 10. A mixing ratio of triethanolamine is not particularly limited. Triethanolamine is used in a ratio of preferably 10 to 80 wt %, more preferably 30 to 50 wt % of the hardness measurement reagent from the viewpoints of suppressing freezing of triethanolamine in the reagent and maintaining the reagent at an appropriate viscosity.

The glycol compound is used as a solvent of the hardness measurement reagent. Examples of the glycol compound include ethylene glycol, propylene glycol, and diethylene glycol. The glycol compound may be used alone or as a mixture of two or more thereof. Of those, ethylene glycol is particularly preferable from the viewpoints of suppressing degradation of the dye and preventing freezing of triethanolamine. A mixing ratio of the glycol compound is not particularly limited. The glycol compound is used in a ratio of preferably 10 to 80 wt %, more preferably 30 to 50 wt % of the hardness measurement reagent from the viewpoint of serving as an antifreeze solution in the reagent.

The pH buffer is used for preventing pH decrease in sample water regardless of a level of an M alkalinity in the sample water and is a combination of amines chosen from primary amines and secondary amines, and a salt of a weak base. Examples of the primary amines include alkylalcohol amine (such as monoethanolamine), linear alkylamine (such as butylamine), cyclic alkylamine (such as cyclohexylamine), aromatic amine (such as aniline), and amino acids. Examples of the secondary amines include alkylalcohol amine (such as diethanolamine), linear alkylamine (such as diethylamine), cyclic amine (such as azacyclohexane [piperidine]), aromatic amine (such as diphenylamine), and amino acids. Of those, alkylalcohol amines (such as monoethanolamine and diethanolamine) are preferable from the viewpoint of coloring stability of the sample water.

Examples of the salt of a weak base include an ammonium salt, a primary amine salt, and a secondary amine salt. Examples of the ammonium salt include ammonium chloride, ammonium acetate, ammonium sulfate, ammonium bromide, and ammonium oxalate. Examples of the primary amine salt include acid salts (such as hydrochlorides, sulfates, acetates, and oxalates) of alkylalcohol amine (such as monoethanolamine), linear alkylamine (such as butylamine), cyclic alkylamine (such as cyclohexylamine), aromatic amine (such as aniline), and amino acids. Examples of the secondary amine salt include acid salts (such as hydrochlorides, sulfates, acetates, and oxalates) of alkylalcohol amine (such as diethanolamine), linear alkylamine (such as diethylamine), cyclic alkylamine (such as azacyclohexane [piperidine]), aromatic amine (such as diphenylamine), and amino acids.

The combination of the amines and the salt of a weak base is not particularly limited. An alkylalcohol amine-ammonium salt is preferably used from the viewpoint of coloring stability in the sample water. Specific examples thereof include monoethanolamine-ammonium chloride and diethanolamine-ammonium chloride. The alkylalcohol amine-ammonium salt may be used alone or as a mixture of two or more thereof. A mixing ratio of the pH buffer is not particularly limited. The pH buffer is used in a ratio of preferably 5 to 50 wt %, more preferably 10 to 40 wt % of the hardness measurement reagent from the viewpoint of preventing inhibition of functions of other components.

The hardness measurement reagent of the present invention may be accordingly mixed with additives such as a masking reagent, a sensitizer, an antidegradant, and an antifoaming agent without inhibiting the effects of the present invention, in addition to the dye, triethanolamine, the glycol compound, and the pH buffer. The masking reagent is used for stabilizing the coloring of the sample water by forming a complex with interfering ions (such as Fe, Mn, and Al) in the sample water, and examples thereof include triethanolamine and KCN. Of those, triethanolamine is preferably used from the viewpoint of safety in draining thereof as wastewater. The sensitizer is used for sensitizing coloring property of the sample water by replacing $Ca^{2+}$ in the sample water by $Mg^{2+}$, and EDTA-Mg is preferably used. The antidegradant is used for preventing degradation of the dye even when the hardness measurement reagent is used in high temperatures of 50° C. or higher, and potassium sorbate is preferably used. The antifoaming agent is used for antifoaming bubbles in the sample water held in a measurement vessel, and a nonionic surfactant (such as polyoxyethylene octylphenyl ether) is preferably used.

The hardness measurement reagent of the present invention can be produced by uniformly mixing the dye, triethanolamine, the glycol compound, the pH buffer, and the additives as required. For example, a uniform hardness measurement reagent can be produced by: adding and mixing a glycol compound, triethanolamine, and additives as required in the order to a uniformly mixed pH buffer; and finally adding and mixing a dye thereto.

The hardness measurement reagent produced as described above can maintain a pH of sample water at about 10 even when the sample water has a high M alkalinity exceeding 100 mg/l, for example. A transmittance spectrum of the sample water having a high M alkalinity exceeding 100 mg/l in a visible region substantially overlaps a transmittance spectrum of water having an M alkalinity of 0 mg/l at any hardness. Thus, the hardness measurement reagent of the present invention can be used for reliable detection of hardness leakage of water having a particularly high M alkalinity. In order to improve detection accuracy, the sample water is preferably measured after measuring conditions such a dye concentration in the hardness measurement reagent, an amount of the hardness measurement reagent added during measuring, and a volume of the sample water to be sampled are determined. To be specific, the sample water preferably contains 0.00024 wt % to 0.0024 wt % of a dye, 0.05 wt % or more of triethanolamine, and 0.012 wt % or more of a pH buffer after the hardness measurement reagent is added to the sample water.

As described above, the hardness measurement reagent of the present invention is particularly suitable for mechanical measuring involving measurement of absorbance or transmittance, but may also be used similarly for visual measuring. Further, in the present invention, any feed water fed to cooling/heating equipment, water in a cooling/heating water system, boiler water, and the like can be used as hardness measuring objects. Thus, not only softened treated water passed through a water softening device but also raw water before passing through the water softening device can be used as hardness measuring objects.

EXAMPLES

Hereinafter, the present invention will be described in more detail by examples, but the present invention is not limited thereto.

(Effect of M Alkalinity Using Conventional Hardness Measurement Reagent)

An effect of an M alkalinity on a transmittance was studied using a conventional hardness measurement reagent, prior to using hardness measurement reagents of Example 1 and Comparative Example 1. First, standard solutions each having a hardness of 2 mg/l and an M alkalinity of 20 to 200 mg/l were prepared. 4.3 ml of each standard solution was added to a measurement cell having a cell length of 10 mm and a cell volume of 4.3 ml. Next, 20 μl of the conventional hardness measurement reagent of formulation 2 in Table 1 was added and mixed into each standard solution, to thereby prepare a measurement solution. A transmittance of each measurement solution at a wavelength of 400 to 800 nm was measured with a spectrophotometer. FIG. 1 shows the obtained transmittance spectra.

TABLE 1

|  | Mixed component | Formulation 1 | Formulation 2 |
|---|---|---|---|
| Composition of hardness measurement reagent (wt %) | Ethylene glycol | 38.7 | 48.7 |
|  | Triethanolamine | 38.7 | 48.7 |
|  | POE | 1 | 1 |
|  | EBT | 0.3 | 0.3 |
|  | EDTA-Mg | 1.3 | 1.3 |
|  | Monoethanolamine | 15 | 0 |
|  | NH$_4$Cl | 5 | 0 |

POE: polyoxyethylene octylphenyl ether

FIG. 1 confirms that a transmittance of a red light of 655 nm tends to decrease with increasing M alkalinity, and a transmittance of a green light of 525 nm tends to increase with increasing M alkalinity. Thus, FIG. 1 reveals that a hue of the sample water generally shifts to a direction of a blue color with increasing M alkalinity in the sample water using the conventional hardness measurement reagent. In mechanical measuring through measurement of a transmittance of the sample water, a transmittance of a red light is generally measured in consideration of measurement sensitivity, measurement accuracy, and the like. The above results reveal that a measured hardness is smaller than an actual hardness with increasing M alkalinity in mechanical measuring through measurement of a transmittance as an index of a hardness using the conventional hardness measurement reagent.

Example 1

Standard solutions each having a hardness of 2 mg/l and an M alkalinity of 0 mg/l or 150 mg/l were prepared. 4.3 ml of each standard solution was added to a measurement cell having a cell length of 10 mm and a cell volume of 4.3 ml. Next, 20 μl of a hardness measurement reagent of formulation 1 in Table 1 was added and mixed into each standard solution, to thereby prepare a measurement solution. A transmittance of each measurement solution at a wavelength of 400 to 800 nm was measured with a spectrophotometer. FIG. 2 shows the obtained transmittance spectra. Further, Table 2 shows the pH values of the two measurement solutions.

Comparative Example 1

A transmittance of each measurement solution was measured in the same manner as that of Example 1 except that a hardness measurement reagent of formulation 2 in Table 1 was used. FIG. 3 shows the obtained transmittance spectra. Further, Table 2 shows the pH values of the two measurement solutions.

TABLE 2

|  | M alkalinity (mg/l) | pH |
|---|---|---|
| Example 1 | 150 | 9.88 |
|  | 0 | 9.91 |
| Comparative Example 1 | 150 | 9.43 |
|  | 0 | 9.95 |

FIG. 2 (Example 1) shows that the transmittance spectrum of the measurement solution having an M alkalinity of 150 mg/l and that of the measurement solution having an M alkalinity of 0 mg/l substantially overlap. FIG. 3 (Comparative Example 1) reveals that the measurement solution having an M alkalinity of 150 mg/l has a decreased transmittance of a red light of 655 nm and an increased transmittance of a green light of 525 nm compared to those of the measurement solution having an M alkalinity of 0 mg/l. Table 2 indicates that the two measurement solutions shown in FIG. 2 have substantially the same pH values. Further, Table 2 indicates that the two measurement solutions shown in FIG. 3 have different pH values, with the measurement solution having an M alkalinity of 150 mg/l having a lower pH than that of the measurement solution having an M alkalinity of 0 mg/l by 0.5 or more. The above results suggest that the two transmittance spectra in FIG. 2 overlap because a pH buffer of monoethanolamine-ammonium chloride assuredly increases the pH of the measurement solution to a target value regardless of the M alkalinity of the sample water.

What is claimed is:

1. A hardness measurement reagent as a one-solution type reagent, comprising: a dye chosen from Eriochrome Black T (EBT) and Calmagite; triethanolamine; a glycol compound; and a pH buffer, wherein the pH buffer comprises a combination of (i.) amines chosen from primary amines and secondary amines and (ii.) a salt of a weak base.

2. A hardness measurement reagent according to claim 1, wherein the salt of a weak base comprises a salt selected from the group consisting of an ammonium salt, a primary amine salt, and a secondary amine salt.

3. A one-solution type hardness measurement reagent comprising: a dye chosen from Eriochrome Black T (EBT) and Calmagite; triethanolamine; a glycol compound; a pH buffer; a sensitizer; and an antifoaming agent, wherein the pH buffer comprises a combination of (i.) amines chosen from primary amines and secondary amines and (ii.) a salt of a weak base.

4. The one-solution type hardness measurement reagent of claim 3, comprising Eriochrome Black T, triethanolamine, ethylene glycol, EDTA-Mg as a sensitizer, polyoxyethylene octylphenyl ether as an antifoaming agent, and a pH buffer comprising monoethanolamine and ammonium chloride.

5. A one-solution type hardness measurement reagent comprising: (a) a dye selected from the group consisting of Eriochrome Black T (EBT) and Calmagite; (b) triethanolamine; (c) a glycol compound selected from the group consisting of ethylene glycol, propylene glycol, and diethylene glycol; and (d) a pH buffer, wherein the pH buffer comprises a combination of (i.) amines chosen from primary amines and secondary amines and (ii.) a salt of a weak base.

* * * * *